(12) United States Patent
Kobayashi et al.

(10) Patent No.: US 6,945,928 B2
(45) Date of Patent: Sep. 20, 2005

(54) ELECTRONIC ENDOSCOPE SYSTEM

(75) Inventors: Hiroyuki Kobayashi, Saitama (JP); Kohei Iketani, Saitama (JP)

(73) Assignee: PENTAX Corporation, Tokyo (JP)

(*) Notice: Subject to any disclaimer, the term of this patent is extended or adjusted under 35 U.S.C. 154(b) by 171 days.

(21) Appl. No.: 10/390,648

(22) Filed: Mar. 19, 2003

(65) Prior Publication Data

US 2003/0179291 A1 Sep. 25, 2003

(30) Foreign Application Priority Data

Mar. 20, 2002 (JP) ................................ P2002-077601

(51) Int. Cl.$^7$ ................................ A61B 1/04
(52) U.S. Cl. ........................ 600/109; 600/173
(58) Field of Search ...................... 600/109, 101, 600/103, 112, 118, 160, 167, 173, 176, 181; 348/65, 72, 74–75

(56) References Cited

U.S. PATENT DOCUMENTS 4,727,418 A * 2/1988 Kato et al. ............... 348/74
5,577,991 A * 11/1996 Akui et al. ............... 600/111
6,322,496 B1 * 11/2001 Iida et al. ............... 600/118
6,621,524 B1 * 9/2003 Iijima et al. ............. 348/584
6,670,983 B2 * 12/2003 Abe ......................... 348/65

* cited by examiner

*Primary Examiner*—John Leubecker
*Assistant Examiner*—Philip R Smith
(74) *Attorney, Agent, or Firm*—Greenblum & Bernstein, P.L.C.

(57) ABSTRACT

An electronic endoscope apparatus is provided that comprises an image-pickup device, an objective optical system, a compensation information storing memory, a mask data storing memory, and an electronic mask compensation processor. The objective optical system forms a subject image on an imaging surface of the image-pickup device. The compensation information storing memory stores compensation information which relates to a misalignment between an in-focus area produced by the objective optical system on the imaging surface, and an effective image sensing area of the image-pickup device. The mask data storing memory stores mask data for an electronic mask operation. The electronic mask compensation processor translates an electronic mask area in accordance with the compensation information.

11 Claims, 7 Drawing Sheets

FIG. 4

| Ax / Ay | 0 | 1 | 2 | 3 | 4 | ... | m-1 | m |
|---|---|---|---|---|---|---|---|---|
| 0 | 0 | 0 | 0 | 0 | 1 | ... | 0 | 0 |
| 1 | 0 | 0 | 0 | 1 | 1 | ... | 0 | 0 |
| 2 | 0 | 0 | 1 | 1 | 1 | ... | 0 | 0 |
| 3 | 0 | 1 | 1 | 1 | 1 | ... | 1 | 0 |
| 4 | 1 | 1 | 1 | 1 | 1 | ... | 1 | 1 |
| ⋮ | ... | ... | ... | ... | ... | ... | ... | ... |
| n-1 | 0 | 0 | 0 | 1 | 1 | ... | 0 | 0 |
| n | 0 | 0 | 0 | 0 | 1 | ... | 0 | 0 |

FIG. 5

|   | 1 | 2 | 3 | 4 | 5 | ... | m-2 | m-1 | m |
|---|---|---|---|---|---|---|---|---|---|
| 1 | 0 0 0 | 0 0 0 | 0 0 0 | 0 0 0 | $Y_{Sx+4\_Sy}$ $Cb_{Sx+4\_Sy}$ $Cr_{Sx+4\_Sy}$ | ... | 0 0 0 | 0 0 0 | 0 0 0 |
| 2 | 0 0 0 | 0 0 0 | 0 0 0 | $Y_{Sx+3\_Sy+1}$ $Cb_{Sx+3\_Sy+1}$ $Cr_{Sx+3\_Sy+1}$ | $Y_{Sx+4\_Sy+1}$ $Cb_{Sx+4\_Sy+1}$ $Cr_{Sx+4\_Sy+1}$ | ... | 0 0 0 | 0 0 0 | 0 0 0 |
| 3 | 0 0 0 | 0 0 0 | $Y_{Sx+2\_Sy+2}$ $Cb_{Sx+2\_Sy+2}$ $Cr_{Sx+2\_Sy+2}$ | $Y_{Sx+3\_Sy+2}$ $Cb_{Sx+3\_Sy+2}$ $Cr_{Sx+3\_Sy+2}$ | $Y_{Sx+4\_Sy+2}$ $Cb_{Sx+4\_Sy+2}$ $Cr_{Sx+4\_Sy+2}$ | ... | $Y_{Sx+m-2\_Sy+2}$ $Cb_{Sx+m-2\_Sy+2}$ $Cr_{Sx+m-2\_Sy+2}$ | 0 0 0 | 0 0 0 |
| 4 | 0 0 0 | $Y_{Sx+1\_Sy+3}$ $Cb_{Sx+1\_Sy+3}$ $Cr_{Sx+1\_Sy+3}$ | $Y_{Sx+2\_Sy+3}$ $Cb_{Sx+2\_Sy+3}$ $Cr_{Sx+2\_Sy+3}$ | $Y_{Sx+3\_Sy+3}$ $Cb_{Sx+3\_Sy+3}$ $Cr_{Sx+3\_Sy+3}$ | $Y_{Sx+4\_Sy+3}$ $Cb_{Sx+4\_Sy+3}$ $Cr_{Sx+4\_Sy+3}$ | ... | $Y_{Sx+m-2\_Sy+3}$ $Cb_{Sx+m-2\_Sy+3}$ $Cr_{Sx+m-2\_Sy+3}$ | 0 0 0 | 0 0 0 |
| 5 | $Y_{Sx\_Sy+4}$ $Cb_{Sx\_Sy+4}$ $Cr_{Sx\_Sy+4}$ | $Y_{Sx+1\_Sy+4}$ $Cb_{Sx+1\_Sy+4}$ $Cr_{Sx+1\_Sy+4}$ | $Y_{Sx+2\_Sy+4}$ $Cb_{Sx+2\_Sy+4}$ $Cr_{Sx+2\_Sy+4}$ | $Y_{Sx+3\_Sy+4}$ $Cb_{Sx+3\_Sy+4}$ $Cr_{Sx+3\_Sy+4}$ | $Y_{Sx+4\_Sy+4}$ $Cb_{Sx+4\_Sy+4}$ $Cr_{Sx+4\_Sy+4}$ | ... | $Y_{Sx+m-2\_Sy+4}$ $Cb_{Sx+m-2\_Sy+4}$ $Cr_{Sx+m-2\_Sy+4}$ | $Y_{Sx+m-1\_Sy+4}$ $Cb_{Sx+m-1\_Sy+4}$ $Cr_{Sx+m-1\_Sy+4}$ | $Y_{Sx+m\_Sy+4}$ $Cb_{Sx+m\_Sy+4}$ $Cr_{Sx+m\_Sy+4}$ |
| ... | ... | ... | ... | ... | ... | ... | ... | ... | ... |
| n-1 | 0 0 0 | 0 0 0 | 0 0 0 | 0 0 0 | $Y_{Sx+4\_Sy+n-1}$ $Cb_{Sx+4\_Sy+n-1}$ $Cr_{Sx+4\_Sy+n-1}$ | ... | 0 0 0 | 0 0 0 | 0 0 0 |
| n | 0 0 0 | 0 0 0 | 0 0 0 | 0 0 0 | $Y_{Sx+4\_Sy+n}$ $Cb_{Sx+4\_Sy+n}$ $Cr_{Sx+4\_Sy+n}$ | ... | 0 0 0 | 0 0 0 | 0 0 0 |

FIG. 8

| | 1 | 2 | 3 | 4 | 5 | ... | m−2 | m−1 | m |
|---|---|---|---|---|---|---|---|---|---|
| 1 | 0 0 0 | 0 0 0 | 0 0 0 | 0 0 0 | Y Sx+4+α_Sy−β<br>Cb Sx+4+α_Sy−β<br>Cr Sx+4+α_Sy−β | ... | 0 0 0 | 0 0 0 | 0 0 0 |
| 2 | 0 0 0 | 0 0 0 | 0 0 0 | Y Sx+3+α_Sy+1+β<br>Cb Sx+3+α_Sy+1+β<br>Cr Sx+3+α_Sy+1+β | Y Sx+4+α_Sy+1+β<br>Cb Sx+4+α_Sy+1+β<br>Cr Sx+4+α_Sy+1+β | ... | 0 0 0 | 0 0 0 | 0 0 0 |
| 3 | 0 0 0 | Y Sx+1+α_Sy+2+β<br>Cb Sx+1+α_Sy+2+β<br>Cr Sx+1+α_Sy+2+β | Y Sx+2+α_Sy+2+β<br>Cb Sx+2+α_Sy+2+β<br>Cr Sx+2+α_Sy+2+β | Y Sx+3+α_Sy+2+β<br>Cb Sx+3+α_Sy+2+β<br>Cr Sx+3+α_Sy+2+β | Y Sx+4+α_Sy+2+β<br>Cb Sx+4+α_Sy+2+β<br>Cr Sx+4+α_Sy+2+β | ... | 0 0 0 | 0 0 0 | 0 0 0 |
| 4 | Y Sx+α_Sy+3+β<br>Cb Sx+α_Sy+3+β<br>Cr Sx+α_Sy+3+β | Y Sx+1+α_Sy+3+β<br>Cb Sx+1+α_Sy+3+β<br>Cr Sx+1+α_Sy+3+β | Y Sx+2+α_Sy+3+β<br>Cb Sx+2+α_Sy+3+β<br>Cr Sx+2+α_Sy+3+β | Y Sx+3+α_Sy+3+β<br>Cb Sx+3+α_Sy+3+β<br>Cr Sx+3+α_Sy+3+β | Y Sx+4+α_Sy+3+β<br>Cb Sx+4+α_Sy+3+β<br>Cr Sx+4+α_Sy+3+β | ... | Y Sx+m−2+α_Sy+3+β<br>Cb Sx+m−2+α_Sy+3+β<br>Cr Sx+m−2+α_Sy+3+β | Y Sx+m−1+α_Sy+3+β<br>Cb Sx+m−1+α_Sy+3+β<br>Cr Sx+m−1+α_Sy+3+β | 0 0 0 |
| 5 | Y Sx+α_Sy+4+β<br>Cb Sx+α_Sy+4+β<br>Cr Sx+α_Sy+4+β | Y Sx+1+α_Sy+4+β<br>Cb Sx+1+α_Sy+4+β<br>Cr Sx+1+α_Sy+4+β | Y Sx+2+α_Sy+4+β<br>Cb Sx+2+α_Sy+4+β<br>Cr Sx+2+α_Sy+4+β | Y Sx+3+α_Sy+4+β<br>Cb Sx+3+α_Sy+4+β<br>Cr Sx+3+α_Sy+4+β | Y Sx+4+α_Sy+4+β<br>Cb Sx+4+α_Sy+4+β<br>Cr Sx+4+α_Sy+4+β | ... | Y Sx+m−2+α_Sy+4+β<br>Cb Sx+m−2+α_Sy+4+β<br>Cr Sx+m−2+α_Sy+4+β | Y Sx+m−1+α_Sy+4+β<br>Cb Sx+m−1+α_Sy+4+β<br>Cr Sx+m−1+α_Sy+4+β | Y Sx+m+α_Sy+4+β<br>Cb Sx+m+α_Sy+4+β<br>Cr Sx+m+α_Sy+4+β |
| ... | ... | ... | ... | ... | ... | ... | ... | ... | ... |
| n−1 | 0 0 0 | 0 0 0 | 0 0 0 | Y Sx+3+α_Sy+n−1+β<br>Cb Sx+3+α_Sy+n−1+β<br>Cr Sx+3+α_Sy+n−1+β | Y Sx+4+α_Sy+n−1+β<br>Cb Sx+4+α_Sy+n−1+β<br>Cr Sx+4+α_Sy+n−1+β | ... | 0 0 0 | 0 0 0 | 0 0 0 |
| n | 0 0 0 | 0 0 0 | 0 0 0 | 0 0 0 | Y Sx+4+α_Sy+n+β<br>Cb Sx+4+α_Sy+n+β<br>Cr Sx+4+α_Sy+n+β | ... | 0 0 0 | 0 0 0 | 0 0 0 |

ELECTRONIC ENDOSCOPE SYSTEM

BACKGROUND OF THE INVENTION

1. Field of the Invention

The present invention relates to an electronic endoscope system. Particularly, the present invention relates to a mask operation for image signals that are obtained by an image-pickup device.

2. Description of the Related Art

In recent years, electronic endoscopes have been widely used as effective devices for instant observation of an internal space, such as the inner wall of digestive organs and the like. An electronic endoscope comprises a flexible conduit (or insertion portion) that is inserted into an organ. At the distal end of the flexible conduit, an image-pickup device, which is associated with an objective lens, is mounted. The image-pickup device feeds image signals of the subject image to an exclusive image-signal processing unit or apparatus, so that the image processor reproduces a color image of the subject on a monitor screen in accordance with the image signals.

The depth of field of the objective lens, which is fixed at the distal end of the flexible conduit, is set relatively deep, so that an image of an internal organ can be captured in-focus over a wide range, even though the focus of the optical system is fixed. Namely, a relatively short focal length is provided for the objective lens. However, when the focal length of the objective lens is short so as to provide a deep depth of field without narrowing the stop, an image on the imaging surface (or image plane) of the image-pickup device becomes strongly blurred as the radial distance from the optical axis increases due to the aberration of the objective lens, such as an astigmatism. Therefore, the outer peripheral region where the strong blur appears is masked, and only the in-focused area, the area on which a clear image is produce, is displayed on a monitor screen.

An example of masking is an optical mask that is arranged at the above outer peripheral area of the imaging surface of the image-pickup device. Namely, the optical mask optically shields the outer peripheral area from the incident light, and image signals output from the masked outer peripheral area are made substantially equal to the black level. Another example of masking is an electronic mask (or mask operation). The electronic mask is achieved by replacing image signals corresponding to the above outer peripheral area of the imaging surface with black level signals in an image-processing unit. In a conventional masking method, an area to be masked (in the following referred to as a masking area) is located at the peripheral area of the in-focus area, and the masking area is previously defined in the design stage by regarding the size of the in-focus area and its position relative to the imaging surface.

Since the flexible conduit of an electronic endoscope is inserted into a narrow space like an organ, the maximum diameter for the conduit is a couple of centimeters at most, so that the size of the image-pickup device and the objective lens is a minimum. These facts give rise to the requirement for precise attachment of the image-pickup device and the objective lens, and for accurately applying the optical mask to the imaging surface of the image-pickup device. Therefore, as a practical matter, the positions of the in-focus area, the imaging area (effective image-sensing area or image-output area), and the masking area are not appropriately aligned as a result of a small relative displacements between the optical axis of the objective lens, the center of the imaging area, and the center of the optical mask. Further, these errors in the alignment are peculiar to each particular electronic endoscope.

Namely, when an electronic endoscope, which is connected to the image-signal processing unit, is changed to a different one, the alignment of the objective lens, the imaging area, and the optical mask is also changed, so that an undesirable part, such as the out-focus area may appear on the monitor.

SUMMARY OF THE INVENTION

Therefore, an object of the present invention is to provide an electronic endoscope apparatus, an electronic endoscope, and an image-signal processing unit that are able to compensate for the effects of a misalignment between an imaging area and an in-focus area in a reproduced image.

According to the present invention, an electronic endoscope apparatus is provided that comprises an image-pickup device, an objective optical system, a compensation information storing memory, a mask data storing memory, and an electronic mask compensation processor.

The image-pickup device has an imaging surface and feeds image signals. The objective optical system forms a subject image on the imaging surface. The compensation information storing memory stores compensation information which relates to a misalignment between an in-focus area produced by the objective optical system on the imaging surface, and an effective image sensing area of the imaging surface. The mask data storing memory stores mask data for an electronic mask operation. The electronic mask compensation processor translates an electronic mask area in accordance with the compensation information.

Further, according to the present invention, an electronic endoscope is provided that comprises an image-pickup device, an objective optical system, and a compensation information storing memory.

The objective optical system forms a subject image on an imaging surface of the image-pickup device. The compensation information storing memory stores compensation information which relates to a misalignment between an in-focus area produced by the objective optical system on the imaging surface, and an effective image sensing area of the imaging surface.

Further, according to the present invention, an image-signal processing unit is provided. The image-signal processing unit is able to connect with an electronic endoscope that comprises an image-pickup device, an objective optical system, and a compensation information storing memory. The objective optical system forms a subject image on an imaging surface of the image-pickup device. The compensation information storing memory stores compensation information which relates to a misalignment between an in-focus area produced by the objective optical system on the imaging surface, and an effective image sensing area of the image-pickup device. The image-signal processing unit comprises a mask data storing memory and an electronic mask compensation processor.

The mask data storing memory stores mask data for an electronic mask operation. The electronic mask compensation processor reads the compensation information from the compensation information storing memory and translates an electronic mask area in accordance with the compensation information.

BRIEF DESCRIPTION OF THE DRAWINGS

The objects and advantages of the present invention will be better understood from the following description, with reference to the accompanying drawings in which:

FIG. 4 schematically illustrates an example of the mask data stored in the ROM;

FIG. 5 schematically illustrates the contents of the component digital signals fed to the secondary image-signal processing circuit when the arrangement of the masked areas is the same as that shown in FIG. 3 and when the mask data of FIG. 4 is used;

FIG. 8 schematically illustrates the contents of the component digital signals fed to the secondary image-signal processing circuit when the position of the image center Ck is separate by $(\alpha,\beta)$ from the principal point Cf, as shown in FIG. 7, and when the mask data of FIG. 4 is used.

DESCRIPTION OF THE PREFERRED EMBODIMENTS

Figure 1:
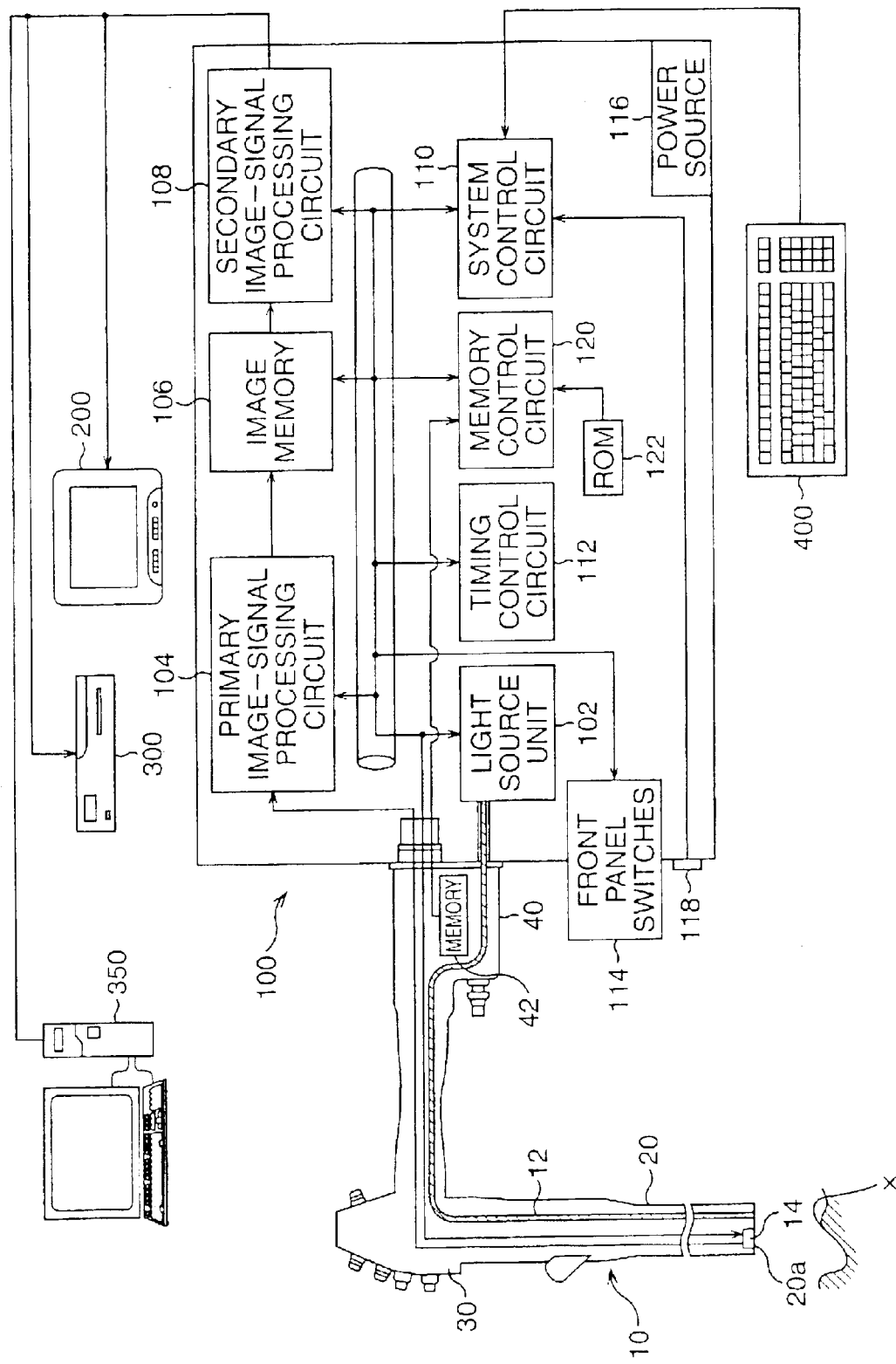
FIG. 1 is a block diagram of an electronic endoscope system of an embodiment of the present invention.

The present invention is described below with reference to the embodiments shown in the drawings.

FIG. 1 is a block diagram of an electronic endoscope system of an embodiment of the present invention. The electronic endoscope apparatus shown in the embodiment of FIG. 1 is constructed so as to convert an optical image of a subject to electrical image signals, and to indicate the subject image on the monitor screen. Further, in the electronic endoscope apparatus, a simultaneous imaging system is applied for reproducing a color image. Namely, an image-pickup device with an on-chip color filter is used to capture each of the color component images, simultaneously. Furthermore, in the electronic endoscope system, image signals may be adapted to the NTSC or PAL standard.

The electronic endoscope apparatus may comprise an electronic endoscope 10 with a flexible conduit 20, an image-processing unit 100, and a monitor 200. The electronic endoscope 10 is detachably connected to an image-signal processing unit 100, and a monitor 200 is also connected to the image-signal processing unit 100.

Inside the electronic endoscope 10, a light guide member 12 (indicated by a hatched portion in the figure) which is comprised of an optical fiber bundle, is arranged. One end of the light guide member 12 is positioned at the distal end 20a of the flexible conduit 20. The other end of the light guide member 12 is optically connected to a light source unit 102, which is inside the image-signal processing unit 100, when the electronic endoscope 10 is attached to the image-signal processing unit 100. Thereby, illumination light from the light source unit 102 is transmitted to the distal end 20a of the flexible conduit 20 through the light guide member 12, so that a subject, such as an organ X in front of the distal end 20a, is illuminated.

Figure 2:
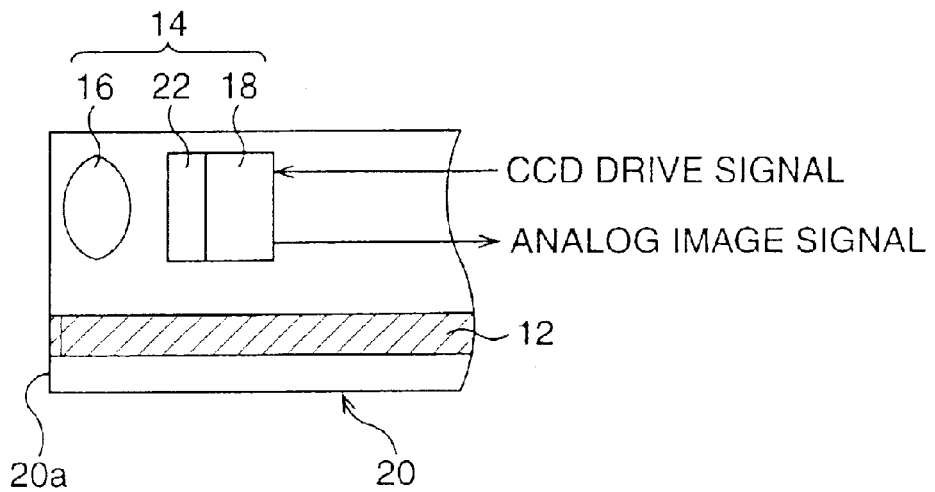
FIG. 2 is a magnified sectional view at the distal end of a flexible conduit or insertion portion of the electronic endoscope.

At the distal end 20a of the flexible conduit 20, an imaging sensor 14, which may comprise a solid-state image-pickup device, such as a CCD 18 shown in FIG. 2, is provided. As shown in the magnified sectional view of FIG. 2, the imaging sensor 14 comprises an objective lens system 16 which is associated with the CCD 18. Further, an optical mask 22 is integrally provided on the imaging surface of the CCD 18, which faces the objective lens. The optical image of the subject, which is illuminated by white illumination light, is produced on the imaging surface of the CCD 18 through the objective lens system 16. A color image is separated into several color components by a complementary color filter (not shown) attached on the imaging surface of the CCD 18, as is well known in the art. The subject image optically formed on the CCD 18 is photo-electrically converted to analog image signals, so that a frame image can be electronically captured by the imaging sensor 14. The analog signals are then readout in turn from the CCD 18 according to CCD drive signals generated by a timing control circuit 112 inside the image-processing unit 100. The outer peripheral area (out-of-focus area), where images are blurred through the objective lens system 16, is shielded from the light by an optical mask 22.

Analog image signals from the imaging sensor 14 are fed to a primary image-signal processing circuit 104 and subjected to processes that are necessary to accommodate the characteristics of the imaging sensor 14 and the optical characteristics of the electronic endoscope 10, such as a clamp process, a sample-hold process, a gamma correction process, a white-balance-correction process, and amplifying process. The image signals are then transformed to digitalized component signals that are composed of luminance signals Y, color difference signals Cb and Cr, and stored in an image memory 106 in turn.

When the digitalized component signals of one frame image are readout from the image memory 106 and fed to a secondary image-signal processing circuit 108, they are converted to analog color video signals, such as NTSC or PAL standard composite video signals which are multiplex signals of the luminance signals, color difference signals, and composite synchronizing signals. The analog color video signals are then output to the monitor 200 from the image-signal processing unit 100, and the subject image is reproduced on the screen of the monitor 200 in accordance with the analog color video signals. Further, the analog color video signals may be output from the image-signal processing unit 100 to an image recorder 300, such as a VCR, so that video image is recorded on a videotape or the like. Furthermore, the analog color video signals are fed to a filing device 350, which may be connected to a personal computer, via an interface (not shown), and may be filed as a still image or a video image.

A keyboard 400 is connected to the system control circuit 110 as an input device, so that a name of a patient is input by using the keyboard 400. The name of the patient, date information from a timer, and any other necessary information are transformed to character pattern signals at the system control circuit 110 and output to the secondary image-signal processing circuit 108. The character pattern signals are then added to the digitalized component signals. Thereby, character information is also indicated on the screen of the monitor 200 with the subject image.

The system control circuit 110 is a microcomputer that controls the whole operation of the image-signal processing unit 100, and comprises a CPU, ROM that stores a program and parameters for executing various routines, and RAM that is for temporally storing data. A timing control circuit 112 that generates synchronizing signals for synchronizing operations at each of the circuits.

The image-signal processing unit has a front panel 114 with a plurality of switches. The switches are for manually adjusting picture quality and illumination intensity, and for setting various modes. Further, the image-signal processing unit 100 has a power source unit 116 that supplies power to each of the circuits in the image-processing unit 100 and the light source unit 102, and a power switch 118 for switching the ON/OFF states of the power source unit 116.

The electronic endoscope 10 has an operating handle 30 that is integrated with the flexible conduit 20. The operating handle 30 is provided with levers and buttons that are for mechanical operations of the flexible conduit 20 and for electrical operations of the system. One end of a flexible coupling tube for connecting the electronic endoscope to the image-signal processing unit 100 is integrally attached to the operating handle 30. At the other end of the flexible coupling tube, a connector unit 40 is attached. The connector unit 40 comprises connector components that are used to connect the electronic endoscope 10 to the image-signal processing unit 100, electrically and optically. The connector 40 also comprises a memory 42 that stores the masking position compensation data peculiar to each of the electronic endoscopes. An example of the memory 42 is EEPROM which is able to rewrite data.

The image-signal processing unit 100 is provided with a mask operation function (electronic mask operation) that is able to clip out only an in-focus area from the subject image displayed on the screen of the monitor 200 and mask the outer peripheral area. The image-signal processing unit 100 comprises a memory control circuit 120 that controls the read/write operations of the digitalized component signals from/to the image memory 106, so that the electronic mask operation is carried out by controlling the readout addresses from the memory control circuit 120 and by outputting video signals in accordance with the address.

In detail, when the main power switch of the image-signal processing unit 100 is turned on, the memory control circuit 120 reads mask data, from the ROM 122, that defines the area, shape, and size to be clipped from the color image which will be reproduced on the screen. The memory control circuit 120 also reads the masking position compensation data from the memory 42 when the electronic endoscope 10 is connected to the image-signal processing unit 100. Thereby, the memory control circuit 120 generates the series of readout addresses based on the mask data and the masking position compensation data. The digitalized component signals, the luminance signals Y and color difference signals Cb and Cr, due to the readout address, are then output to the secondary image-signal processing circuit 108.

Figure 3:
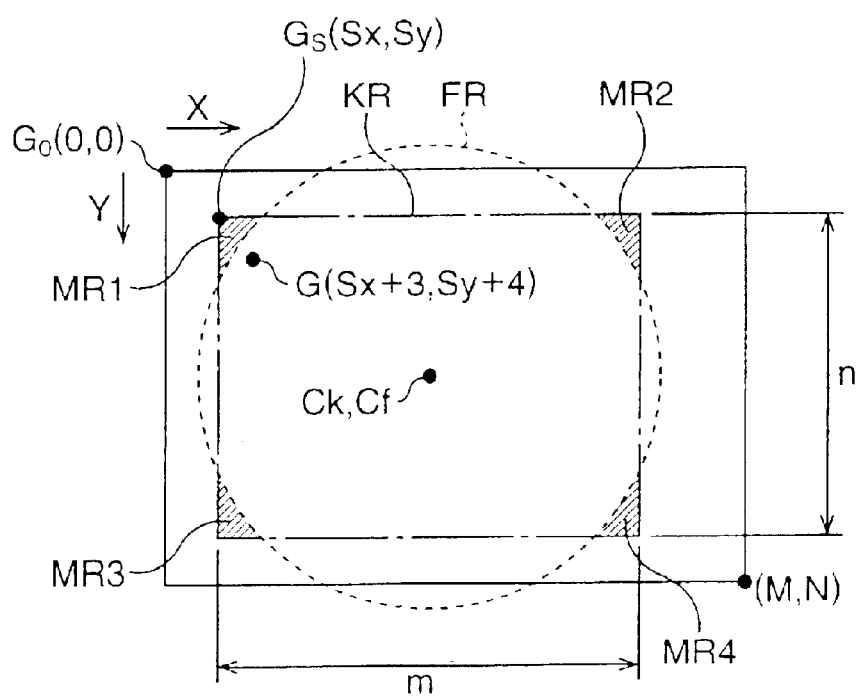
FIG. 3 schematically illustrates the arrangement of the photosensitive area, the imaging area, the in-focus area, and the blackout area due to the optical mask.

With reference to FIG. 3, the principle of the masking process is described. FIG. 3 schematically illustrates the imaging surface of the CCD 18, namely the arrangement of the photosensitive area (area in which photo sensitive elements are arranged), the imaging area (or effective image sensing area) of the imaging surface, the in-focus area on the imaging surface of the imaging surface, and the blackout area due to the optical mask.

The CCD 18 is comprised of numerous pixels that are two-dimensionally arranged in a matrix on the imaging surface, and has M pixels in the horizontal direction (indicated by an arrow X in the figure) and N pixels in the vertical direction (indicated by an arrow Y in the figure). Since the pixels are regularly arranged in matrix, the position of an arbitrary pixel G in the photosensitive area of the imaging surface is represented by the coordinates or ordinate pair (i,j) with respect to the origin (0,0) at the upper-left pixel of the imaging surface or the photosensitive area. The parameter "i" represents the number of pixels in the X direction from the origin $G_O$ (0,0) to the pixel, and satisfies the condition $0 \leq i \leq M$. Further, the parameter "j" represents the number of pixels in the Y direction from the origin $G_O$ (0,0) to the pixel, and satisfies the condition $0 \leq j \leq N$.

On the imaging surface of the CCD 18, only a part of the whole pixel area or the photosensitive area is used for the image capturing. Namely, only m×n ($m \leq M$, $n \leq N$) pixels in the rectangular imaging area KR (effective image sensing area), which is surrounded by the one dot broken line in the figure, can output image signals corresponding to a subject image. The pixels in the area surrounding the imaging area KR are previously masked in the manufacturing process of the CCD, so that the signals from this masked area are only used to define the black level. The position of the imaging area KR in the photosensitive area is represented on the basis of the coordinates (Sx,Sy) with respect to the origin $G_O$, which corresponds to the readout-starting pixel $G_S$. Here, the readout-starting pixel $G_S$ is the upper-left pixel of the imaging area KR. Although the component digital signals are stored in the image memory 106 of the image-signal processing unit 100 for every M×N pixels in the CCD 18, only the signals corresponding to the m×n pixels within the imaging area KR are output to the secondary image-signal processing circuit 108. Namely, the readout operation from the image memory 106 is started from an address corresponding to the readout-starting pixel $G_S$.

Here, an area where the objective lens system 16 can produce a clear image or an in-focus image is referred to as the in-focus area FR (a circular area surrounded with a broken line in the figure). The objective lens system 16 is disposed at a position where the in-focus area FR substantially overlaps the imaging area KR as much as possible and where the principal point Cf (the intersection between the optical axis and the imaging surface) substantially coincides with the image center Ck of the imaging area KR as much as possible. The optical mask 22 is arranged so as to shield the outside of the in-focus area FR. Namely, the blackout areas MR1 to MR4 (each of the areas has a triangular like shape indicated with hatched portions) are formed in each corner of the imaging area KR. These areas are positioned inside the imaging area KR and outside the in-focus area FR. Therefore, the blackout areas MR1 to MR4 are shielded from the light by the optical mask 22, and the signals, due to the black current, output form these areas are about the level of black level signals. However, for various reasons the signals due to the black current are not stable and include noise components.

The image-signal processing unit 100 readouts component digital signals from the image memory 106 to the secondary image-signal processing circuit 108, except the component digital signals corresponding to the blackout areas MR1–MR4. Instead of the signals corresponding to the blackout areas MR1–MR4, mask color component digital signals (e.g. background color signals, more specifically, black level signals) are output to the secondary image-signal processing circuit 108. Namely, the component digital signals for the blackout area MR1–MR4 are replaced by the mask color component digital signals; thereby the electronic mask operation is achieved. The information of the electronic mask operation, such as the mask data that indicate the positions of the pixels to be replaced by the mask color component digital signals, is stored in the ROM 122.

FIG. 4 schematically illustrates an example of the mask data stored in the ROM 122. For convenience, the mask data array in the memory is described in a two-dimensional arrangement, which coincides with the arrangement of the pixels in the imaging area KR. The mask data are provided for each of the m×n pixels in the imaging area KR, so that there is a one-to-one correspondence between the mask data and the m×n pixels. Each of the mask data, which corresponds to a pixel of the imaging area KR, is referred to as a two-dimensional array [Ax,Ay] that corresponds to the position or the coordinates of each pixel with respect to the readout-starting pixel. Namely, the index Ax indicates the position of the horizontal direction in the imaging area KR and the index Ay indicates the position of the vertical direction in the imaging area KR, with respect to the readout-starting pixel $G_S$. For example, the mask data [0,0] corresponds to the readout-starting pixel $G_S$ (Sx,Sy) at the upper-left position of the imaging area KR, and the mask data [3,4] represents the pixel G (Sx+3,Sy+4) which is at the fourth pixel in the X direction and the fifth pixel in the Y direction with respect to the readout-starting pixel $G_S$ (see FIG. 3). Note that the address of the image data (component digital signals) of the pixel corresponding to a mask data [Ax,Ay] can be easily derived from a simple arithmetic calculation, so that the actual address control operation can be carried out with reference to the indexes Ax and Ay.

Each of the mask data (an array element) is assigned with either the numbers "1" or "0" When a mask data is "1", the memory control circuit 120 readouts the component digital signals of the pixel, which corresponds to the above mask data, from the image memory 106 and outputs the signals to the secondary image-signal processing circuit 108. However, when a mask data is "0", the memory control circuit 120 does not readout the component digital signals from the image memory 106, instead the circuit 120 outputs the mask color component digital signals to the secondary image-signal processing circuit 108. For example, the mask data [0,0] in FIG. 4 is "0", so that the mask color component digital signals are output to the secondary image-signal processing circuit 108 for the upper-left pixel $G_S$ (Sx,Sy) of the imaging area KR. Further, the mask data [3,4] is "1", so that the component digital signal from the image memory 106 is output to the secondary image-signal processing circuit 180 for the pixel G (Sx+3,Sy+4).

FIG. 5 schematically illustrates the contents of the component digital signals fed to the secondary image-signal processing circuit 108 when the mask data of FIG. 4 is used. In FIG. 5, the series of the component digital signals is described in a two-dimensional arrangement which corresponds to the pixel arrangement in the imaging area KR. Note that, the suffixes of the luminance signals Y and the color difference signals Cb and Cr, which are the components of the component digital signals, indicate the position of the corresponding pixels in the X and Y directions. For example, the each value of the luminance signal Y and the color difference signals Cb and Cr in the first column of the third line is "0". Further, the values of the luminance signal Y and the color difference signals Cb and Cr in the fifth column of the third line are $Y_{Sx+4\_Sy+2}$, $Cb_{Sx+4\_Sy+2}$, and $Cr_{Sx+4\_Sy+2}$, respectively, which are readout from the pixel G (Sx+4,Sy+2).

Figure 6:
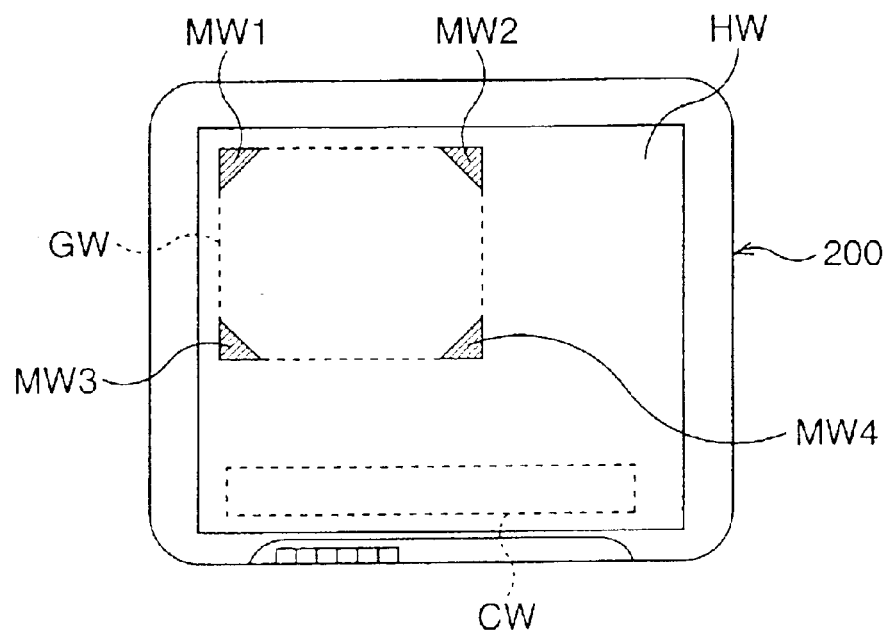
FIG. 6 schematically shows the image displayed on the screen of the monitor when the mask data of FIG. 4 is used.

FIG. 6 schematically shows the image displayed on the screen of the monitor 200 when the mask data of FIG. 4 is used. Within the screen, an image indicating area GW and a background area HW including a character-information indicating area CW are arranged. The image indicating area GW is an area for indicating the color image of the subject obtained by the electronic endoscope 10. The character-information indicating area CW is an area for indicating character information, such as a date, a name of a patient, and the like. Electronic mask areas MW1, MW2, MW3, and MW4 are arranged at the four corners of the image indicating area GW. The electronic mask areas MW1, MW2, MW3, and MW4 are always maintained at the mask color, which may be equivalent to the background color in the background area HW. Each of the electronic mask areas MW1, MW2, MW3, and MW4 is an isosceles right-angle triangle with the length of its two equivalent sides being four pixels of the CCD 18. Due to these electronic mask areas MW1–MW4, the areas covered with the optical mask 22, which may include noise, do not appear on the screen, and only a clear image of the subject within the in-focus area is obtained all the time.

As described above, by determining the values of the mask data corresponding to each of the pixels in the electronic mask areas MW1–MW4 as "0", the electronic mask can be applied to areas that have substantially the same area and shapes as the areas which are masked by the optical mask 22. Note that, any shape or size can be chosen for the electronic mask, provided that the mask covers the electronic mask areas MW1–MW4, and is not restricted to the present embodiment.

As in the example described with reference to FIG. 3, when the image center Ck of the CCD 18 or the imaging area KR coincide with the principal point Cf of the objective lens system 16 or the in-focus area FR (hereinafter, the principal point Cf is assumed as being substantially equal to the center of the optical mask 22) the coordinates (i,j) of a pixel G that correspond to a mask data [Ax,Ay] are obtained from the coordinates (Sx,Sy) of the readout-starting pixel $G_S$ and the indexes Ax and Ay of the mask data together with the following Eqs. (1) and (2).

$$i = Sx + Ax \quad (1)$$

$$j = Sy + Ay \quad (2)$$

The image data for all of the pixels in the photosensitive area are stored in the image memory 106 in series which starts from the data corresponding to the pixel at the origin $G_O$ (0,0), so that the address of the image data (component digital signals) corresponding to the mask data [Ax,Ay] can be easily derived from the coordinates (i,j) which are calculated by Eqs. (1) and (2).

However, in the assembling process of the electronic endoscope 10, it is extremely hard to make sure the image center Ck, the principal point Cf, and the center of the optical mask 22 precisely coincide, so that assembling operations for the precise alignment of these three centers require time and labor. Thereby, in the actual assembling operations, there exist some errors in the above alignment when the CCD 18, the objective lens system 16, and the optical mask 22 are assembled. Namely, each electronic endoscope has peculiar alignment errors.

Figure 7:
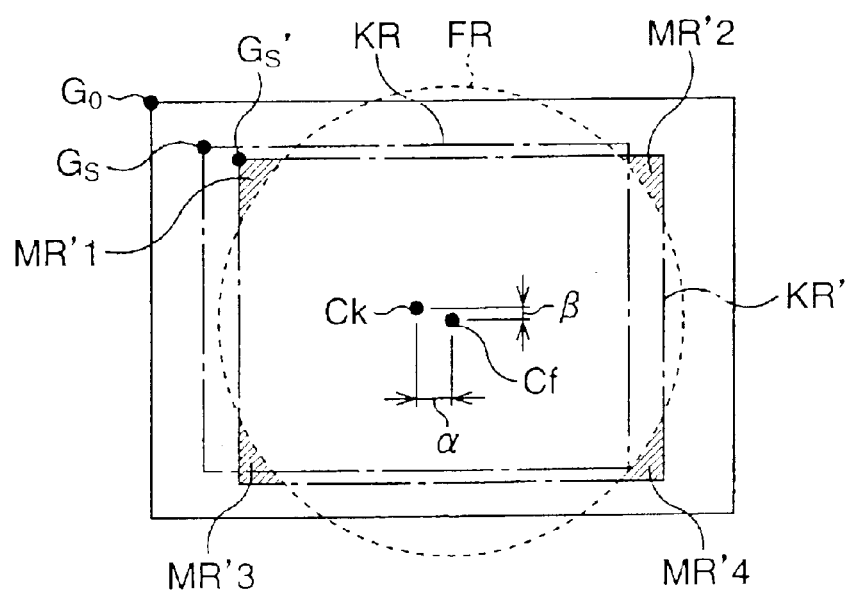
FIG. 7 schematically illustrates the arrangement of the photosensitive area, the imaging area, the in-focus area, and the blackout area due to the optical mask, when the in-focus area is misaligned from the imaging area.

For example, as shown in FIG. 7, when the principal point Cf is undesirably displaced from the image center Ck by α pixels to the X direction and β pixels to the Y direction, in the reproduced color image of a subject on the screen of monitor 200 are displaced from the center of the image indicating area GW by the displacement (α,β) of the principal point Cf. Namely, the area of the optical mask 22 may project out from the electronic mask and some of the out-of-focus image areas may be displayed on the screen.

Accordingly, in the present embodiment, a displacement (α,β) of the principal point Cf from the image center Ck for each electronic endoscope 10 is previously measured, so that the readout position of the component digital signals and the position of the electronic mask, which are based on the mask data stored in the ROM 122, are translated in accordance with the displacement $(\alpha,\beta)$. The above displacement $(\alpha,\beta)$ is stored in the memory 42 of the electronic endoscope 10 as the mask position compensation data (compensation information), and is associated with the product name or serial number of the electronic endoscope 10 stored in the memory 42. The mask position compensation data is readout from the memory 42 when the electronic endoscope 10 is connected to the image-signal processing unit 100, and then fed to the memory control circuit 120. Note that, in place of the displacement $(\alpha,\beta)$, the absolute position of the electronic mask area may be used as the compensation information.

The memory control circuit 120 calculates the coordinates (i,j) of the pixel G that corresponds to a mask data [Ax,Ay] from the coordinates (Sx,Sy) of the readout-starting pixel $G_S$, the indexes Ax and Ay of the mask data, and the mask position compensation data $(\alpha,\beta)$ obtained from the memory 42. Namely, Eqs. (1) and (2) are modified to form the following Eqs. (3) and (4).

$$i = Sx + Ax + \alpha \quad (3)$$

$$j = Sy + Ay + \beta \quad (4)$$

Thereby, the position readout-starting pixel $G_S$ is corrected by Eqs. (3) and (4), so that the readout operations for the image memory 106 starts from an address corresponding to the pixel $G_S'$ $(Sx+\alpha, Sy+\beta)$ which is separate from the pixel $G_S$ by $\alpha$ pixels in the X direction and $\beta$ pixels in the Y direction. Namely, the component digital signals of a compensated imaging area KR' (image output area), the area that is obtained by translating the imaging area KR of m×n pixels in accordance with the mask position compensation data, are readout from the address corresponding to the corrected readout-starting pixel Gs' of the image memory 106. Note that, in accordance with the mask data from the ROM 122, the component digital signals in the area corresponding to the electronic mask area MR'1–MR'4 are replaced by the mask color component digital signals.

FIG. 8 schematically illustrates the contents of the component digital signals fed to the secondary image-signal processing circuit 108 when the position of the image center Ck is separated by $(\alpha,\beta)$ from the principal point Cf, as shown in FIG. 7, and when the mask data of FIG. 4 is used. Each of the readout address, corresponds to the pixel of which coordinates are shifted $(\alpha,\beta)$, so that the values of the luminance signal Y and the color difference signals Cb and Cr for the pixel in the first column of the fifth line are $Y_{Sx+\alpha\_Sy+4+\beta}$, $Cb_{Sx+\alpha\_Sy+4+\beta}$, and $Cr_{Sx+\alpha\_Sy+4+\beta}$, respectively, which are obtained from the pixel $G(Sx+\alpha, Sy+4+\beta)$. Further, the values of the luminance signal Y and the color difference signals Cb and Cr for the pixel in the fifth column of the third line are $Y_{Sx+4+\alpha\_Sy+2+\beta}$, $Cb_{Sx+4+\alpha\_Sy+2+\beta}$, and $Cr_{Sx+4+\alpha\_Sy+2+\beta}$, respectively, and are obtained from the pixel $G(Sx+4+\alpha, Sy+2+\beta)$.

Accordingly, as shown in the example in FIG. 7, when the image center Ck and the principal point Cf are separated by $(\alpha,\beta)$ the areas covered with the optical mask 22, which may include noise, do not appear on the screen. Only a clear image of the subject in the in-focus area is obtained by translating the imaging area KR and the electronic mask areas MR1–MR4 to the compensated imaging area KR' and the compensated electronic mask areas MR'1–MR'4 for the displacement $(\alpha,\beta)$.

Figure 9:
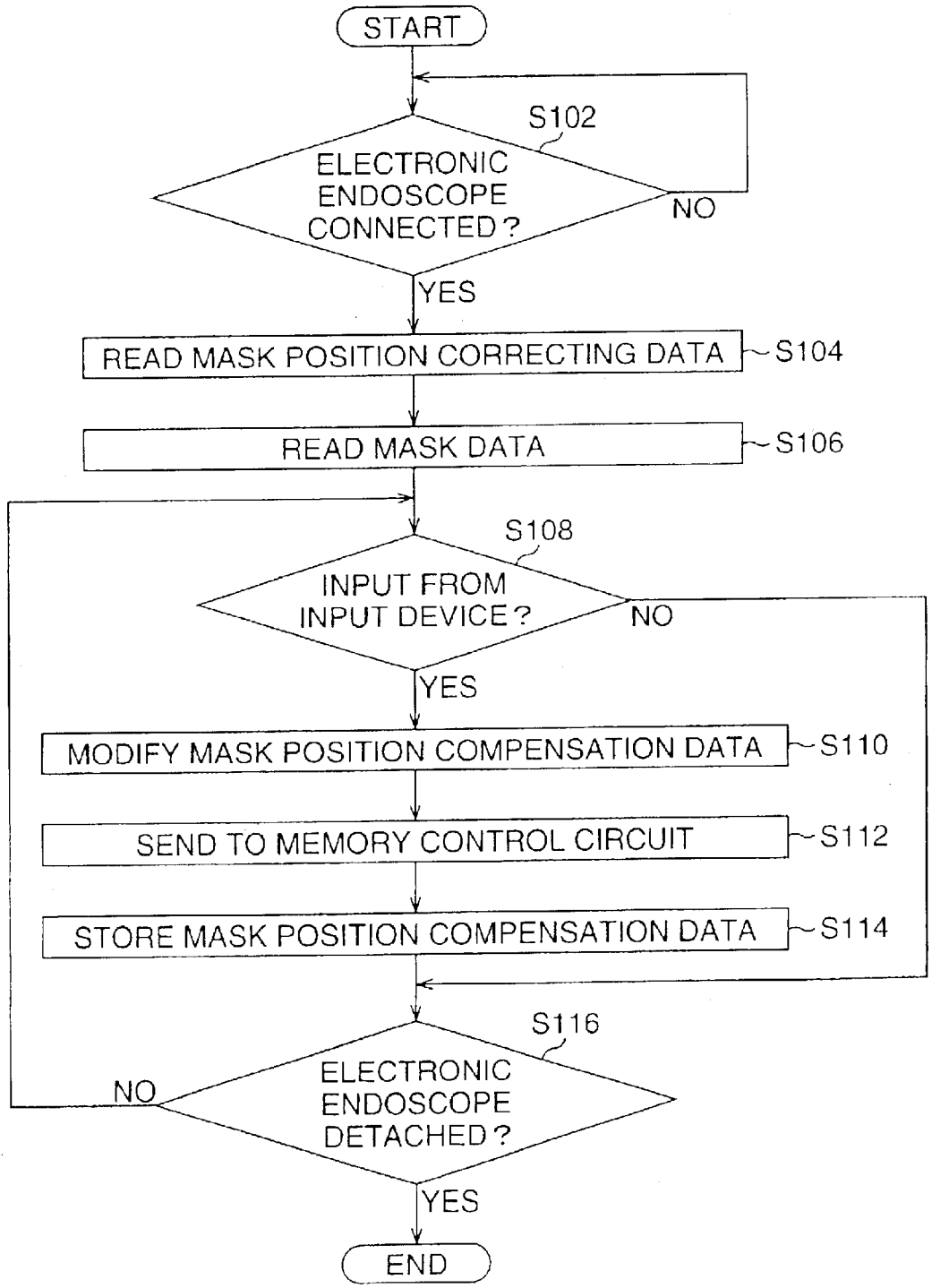
FIG. 9 is a flowchart of the mask operation process carried out in the system control circuit.

FIG. 9 is a flowchart of the mask operation process of the present embodiment carried out in the system control circuit 110. The mask operation process starts when the main power switch 118 on the image-signal processing unit 100 is depressed.

In Step S102, whether the electronic endoscope 10 is connected to the image-signal processing unit 100 is determined. The determination in Step S102 is repeated until the electronic endoscope 10 is connected to the image-signal processing unit 100. When the electronic endoscope 10 is connected to the image-signal processing unit 100, the process proceeds to Step S104 and the mask position compensation data stored in the memory 42 of the electronic endoscope 10 is input to the memory control circuit 120. Then in Step S106, the mask data stored in the ROM 122 is input to the memory control circuit 120. Thereby, the control of the image memory 106 starts in the memory control circuit 120. Namely, the readout address for the compensated imaging area KR' and the correspondence between the mask data and the address in the image memory 106 is established in accordance with the mask position compensation data.

In Step S108, whether an instruction for modifying the mask position compensation data is input from the keyboard 400 is determined. When the modification instruction exists, the mask position compensation data is modified due to the input from the keyboard 400 in Step S110. The modification of the mask position compensation data may be carried out by using the cursor keys with reference to the mask position displayed on the monitor 200 or may be carried out by means of inputting the coordinates of the masking position, such as the start position and end position. Note that, the input of the modification instruction for the mask position compensation data may be enabled when a certain combination of keys input (e.g. password input) is carried out, further it can be carried out by exclusive switches attached to the front panel 114.

When the modification of the mask position compensation data ends, the modified mask position compensation data are input to the memory control circuit 120 in Step S112. Then in Step S114, the modified mask position compensation data are stored in the memory 42 of the electronic endoscope 10. Thereby, the mask position compensation data stored in the memory 42 is replaced by the modified mask position compensation data, so that the modified data is readout when the electronic endoscope 10 is connected to the image-signal processing unit 100 at a later time.

When Step S114 ends or when it is determined, in Step S108, that there is no instruction for modifying the mask position compensation data, Step S116 is carried out. Namely, whether the electronic endoscope 10 is detached from the image-signal processing unit 100 is determined. When it is determined that the electronic endoscope 10 is still connected to the image-signal processing unit 100, the process returns to Step S108 and the succeeding steps are repeated. On the other hand, when it is determined that the electronic endoscope is detached from the image-signal processing unit 100 in Step S116, the mask operation process ends.

As described above, according to the electronic endoscope apparatus and system of the present embodiment, the electronic mask position can be shifted or translated depending on the displacement between the image center and the principal point. Thereby, an in-focused clear subject image without a blur or noise due to black current is obtained at all the time, even though there exists an individual difference between electronic endoscopes. Further, the mask position compensation data for determining the amount of displacement for the mask position can be modified by a user. Further, since the memory 42 for storing the mask position compensation data is provided for the electronic endoscope 10, there is no need for readjusting the mask position even when the electronic endoscope 10 is connected to a different image-signal processing unit. Furthermore, the mask position compensation data are automatically readout from the memory 42 when the electronic endoscope 10 is connected to the image-signal processing unit 100, so that the mask position is easily corrected without being noticed by a user.

Note that, although the simultaneous imaging system is adopted in the present embodiment, the sequential imaging system can be also applied. In this case, the R, G, B color image for one frame are temporally stored in the image memory.

In the present embodiment, the optical system is provided with an optical mask, however, the optical mask can be excluded. Further, in the present embodiment, it is assumed that the principal point and the center of the optical mask are positioned at the same point, the present invention can also be applied when the principal point and the center of the optical mask are misaligned.

Further still, in the present embodiment, the electronic masks are only provided to the areas corresponding to each corner of the imaging area, however, the electronic mask can be provided for the area surrounding the in-focus area. In this case, only the electronic mask area is translated depending on the displacement of the principle point and the translation of the imaging area is not required.

Although the embodiments of the present invention, have been described herein with reference to the accompanying drawings, obviously many modifications and changes may be made by those skilled in this art without departing from the scope of the invention.

The present disclosure relates to subject matter contained in Japanese Patent Application No. 2002-077601 (filed on Mar. 20, 2002), which is expressly incorporated herein, by reference, in its entirety.

What is claimed is:

1. An electronic endoscope apparatus, comprising:
   an image-pickup device that has an imaging surface and that transmits image signals;
   an objective optical system that forms a subject image on said imaging surface;
   a compensation information memory that stores compensation information which relates to a misalignment between an in-focus area produced by said objective optical system on said imaging surface, and an effective image sensing area of said imaging surface;
   a mask data memory that stores mask data for an electronic mask operation;
   an electronic mask compensation processor that translates an electronic mask area in accordance with said compensation information;
   an electronic endoscope that comprises said image-pickup device, said objective optical system, and said compensation information memory; and
   an image-signal processing unit that comprises said mask data memory and said electronic mask compensation processor;
   wherein said electronic endoscope is detachable from said image-signal processing unit.

2. An apparatus according to claim 1, further comprising an electronic mask operation processor that performs said electronic mask operation for said image signals in accordance with the translated electronic mask area.

3. An apparatus according to claim 1, wherein said compensation information is read from said compensation information memory and transmitted to said electronic mask compensation processor when said electronic endoscope is attached to said image-signal processing unit.

4. An apparatus according to claim 1, further comprising an image output area compensation processor that translates an image output area which corresponds to said effective image sensing area in accordance with said compensation information.

5. An apparatus according to claim 1, further comprising an electronic mask position modifying processor that is configured to modify said compensation information.

6. An apparatus according to claim 1, wherein said image signals corresponding to said electronic mask area are replaced by signals of a background color.

7. An apparatus according to claim 1, wherein said compensation information comprises relative displacement information of a principal point of said objective optical system from a center of said effective image sensing area.

8. An apparatus according to claim 1, wherein said electronic mask area covers at least part of an area outside said in-focus area.

9. An apparatus according to claim 8, wherein said electronic mask area is within an inner area of said effective image sensing area.

10. An image-signal processing unit that is configured for connection with an electronic endoscope that comprises an image-pickup device, an objective optical system that forms a subject image on an imaging surface of said image-pickup device, and a compensation information memory that stores compensation information which relates to a misalignment between an in-focus area produced by said objective optical system on said imaging surface and an effective image sensing area of said image-pickup device;
    said image-signal processing unit, comprising:
    a mask data memory that stores mask data for an electronic mask operation;
    an electronic mask compensation processor that reads said compensation information from said compensation information memory and translates an electronic mask area in accordance with said compensation information;
    wherein said electronic endoscope is detachable from said image-signal processing unit.

11. An electronic endoscope apparatus, comprising:
    an image-pickup device that has an imaging surface that transmits image signals;
    an objective optical system that forms a subject image on said imaging surface;
    a compensation information memory that stores compensation information which relates to a misalignment between an in-focus area produced by said objective optical system on said imaging surface, and an effective image sensing area of said imaging surface;
    a mask data memory that stores mask data for an electronic mask operation;
    an electronic mask compensation processor that translates an electronic mask area in accordance with said compensation information; and
    an image output area compensation processor that translates an image output area which corresponds to said effective image sensing area in accordance with said compensation information.

* * * * *